United States Patent
Combourieu et al.

Patent Number: 4,803,219
Date of Patent: Feb. 7, 1989

[54] 1,3-PROPANEDIAMINE DERIVATIVES AND ANTIAUHYTHNIC PHARMACEUTICAL COMPOSITION CONTAINING THEM

[75] Inventors: Michel Combourieu; Nadine Simbille; Marie-Paule Landes, all of Aurillac; Yvon Bernet, Jussac, all of France

[73] Assignee: RIOM Laboratories C.E.R.M., Riom, France

[21] Appl. No.: 76,082

[22] Filed: Jul. 21, 1987

[30] Foreign Application Priority Data

Jul. 22, 1986 [FR] France .................. 86 10638

[51] Int. Cl.$^4$ ............ A61K 31/34; C07D 307/81
[52] U.S. Cl. ........................ 514/469; 549/467
[58] Field of Search ............ 549/467; 514/469

[56] References Cited

U.S. PATENT DOCUMENTS 4,059,621 11/1977 Vincent et al. .............. 544/106

OTHER PUBLICATIONS

Remington's Pharmaceutical Sciences, Gennaro et al., Editor, 17th Edition, p. 859 (1985).
Chemical Abstracts, vol. 69, No. 25, pp. 9955–9956, Item #106373P (1968).
Wagner et al., Synthetic Org. Chem.–Wiley, pp. 566 and 567 (1953). Fieser and Fieser, Advanced Org. Chem.–Reinhold, pp. 85–88 (1961).

Primary Examiner—John M. Ford
Assistant Examiner—Bernard I. Dentz
Attorney, Agent, or Firm—William M. Blackstone

[57] ABSTRACT

N,N-dimethyl-N'-benzoyl-N'-(2,3-dihydrobenzofuran-2-ylmethyl)1,3-propanediamine of formula:

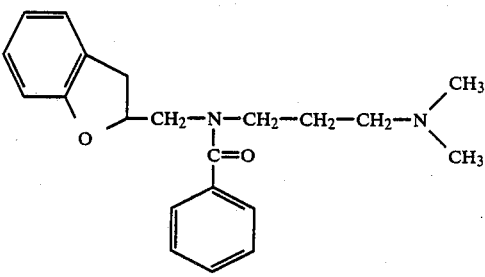

and its pharmaceutically acceptable salts, in racemic form or in the form of enantiomers, which compounds have anti-arrhythmic properties.

5 Claims, No Drawings

1,3-PROPANEDIAMINE DERIVATIVES AND ANTIAUHYTHNIC PHARMACEUTICAL COMPOSITION CONTAINING THEM

The present invention relates to 1,3-propanediamine derivatives and more particularly to N,N-dimethyl-N'-benzoyl-N'-(2,3-dihydrobenzofuran-2-ylmethyl)-1,3-propane-diamine in racemic form or each of its enantiomers or mixtures thereof, as well as their pharmaceutically acceptable salts.

These compounds correspond to the following formula:

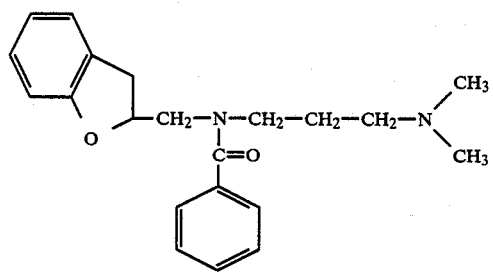

The invention also relates to the processes for preparing the said compounds and the pharmaceutical compositions which are useful in the treatment of disorders of rhythm.

Many benzofuran derivatives are already known, especially derivatives substituted at position 2 with an alkylamino chain. For example, the publication of TOYOSHIMA S., HIROSE N. et al. [Yakugaku Zasshi 88 (5), 503–512 (1968)] describes various benzofuran derivatives; one of these derivatives corresponds to the non-benzoylated compounds of the invention and possesses in particular coronary vasodilatory activity.

The compounds of the invention possess, in contrast, useful anti-arrhythmic properties, while having no effect on the other haemodynamic parameters; they are, in particular, devoid of coronary vasodilatory activity.

The compounds may be prepared by any method known for the preparation of analogous compounds. In particular, the compounds of the invention may be prepared by benzoylation of a compound of formula II:

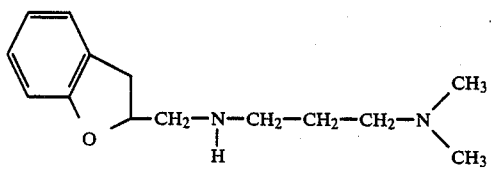

or a salt thereof.

The said benzoylation is preferably carried out with a reactive benozyl derivative such as benzoylhalide (e.g. benzoylchloride or benzoylbromide) or a benzoic acid ester or anhydride but may also be carried out with benzoic acid in the presence of a dehydrating agent such as dicyclohexylcarbodiimide or other carbodiimides.

Using a reactive benzoyl derivative the reaction is preferably carried out in an organic solvent in the presence of an alkaline substance such as triethylamine.

Where the starting compound of formula II is one of the optical enantiomers, the resulting compound is obviously the optical enantiomer of formula I. Where the starting product II is racemic, the resulting compound of formula I is also racemic.

The racemic compound of formula I may be resolved by any method known for the resolution of racemic mixtures.

Usually the racemic base of formula I is resolved with the aid of an optically active carboxylic acid. More particularly the racemic base I may be converted to the tartaric acid salt, from which it is possible, after the customary recrystallisations, to regenerate either the racemic base or the laevorotatory or dextrorotatory isomers, depending on whether (R,S)-, (R,R)- or (S,S)-tartaric acid is used.

The starting diamine of formula II can be prepared according to known processes; for example starting from 2-allylphenol, which is then converted to 2,3-dihydrobenzofuran-2-yl-methanol by the action of a peracid and subsequently to the tosylate by the action of para-toluene-sulphonyl chloride, the said tosylate then being reacted with 3-(dimethylamino)-propylamine to give N,N-dimethyl-N'-(2,3-dihydro-benzofuran-2-ylmethyl)-1,3-propanediamine.

The preparation of the compounds of the invention is illustrated in greater detail by the examples below.

Preparation of N,N-dimethyl-N'-(2,3-dihydrobenzofuran-2-ylmethyl)-1,3-propanediamine In a reactor, 200 g (1.49 mol) of 2-allylphenol was dissolved in 2 l of methylene chloride and 309 g (1.79 mol) of meta-chloroperbenzoic acid were added with the mixture maintained stirred at 0° C., and then at room temperature until the 2-allylphenol had disappeared.

To the solution of 2,3-dihydrobenzofuran-2-ylmethanol, 150.4 g (0.9 mol) of para-toluenesulphonyl chloride were added while the mixture was maintained stirred for 4 hours at room temperature. After evaporation, purification and recrystallisation in absolute ethanol, 197 g of tosylate, of melting point 68°–70° C., were obtained.

Finally, 23.5 g (0.075 mol) of the above tosylate and 38.6 g (0.378 mol) of 3-(dimethylamino)propylamine were suspended in 150 ml of butanol, and the mixture was brought to reflux until the tosylate had disappeared.

After the solvent and then the excess 3-(dimethylamino)propylamine had been evaporated, the residue was taken up in ethyl ether, washed with water, dried over sodiumsulphate, filtered, evaporated to dryness and then distilled under reduced pressure, and 11.4 g of the expected diamine, of boiling point 140°–148° C. under 50 Pa, were obtained.

EXAMPLE 1

Racemic N,N-dimethyl-N'-benzoyl-(2,3-dihydro-benzofuran-2-ylmethyl)-1,3-propanediamine In a 250-ml three-necked flask, 10.6 g (0.045 mol) of the above diamine were dissolved in 100 ml of methylene chloride and 6.8 g (0.0675 mol) of triethylamine were added, 6.4 g (0.045 mol) of benzoyl chloride were then introduced dropwise and the mixture was maintained stirred for ¼ hour at room temperature, and 0.64 g of benzoyl chloride was then added to complete the benzoylation. The reaction medium was diluted with methylene chloride, and the organic phase was washed with 5% strength NaOH solution and then with water and dried over sodiumsulphate.

After filtration and evaporation to dryness, 15.2 g of crude base were obtained in the form of a thick oil which was treated with tartaric acid.

In a 250-ml round-bottomed flask, 5 g of the crude base obtained above were dissolved in a minimum of absolute ethanol, 2.2 g of (R,S)-tartaric acid dissolved in a minimum of absolute ethanol were then added, and the mixture was brought to −5° C. and allowed to return to room temperature. After filtration and washing with absolute ethanol, the precipitate formed was dried under vacuum and 6.2 g of (R,S)-tartrate, of melting point 131.2° C. were obtained. The base regenerated from this tartrate shows no rotatory power.

EXAMPLE 2

(R)-N,N-dimethyl-N'-benzoyl-N'-(2,3-dihydro-benzofuran-2-ylmethyl)1,3-propanediamine By working as described in Example 1, but starting with 5 g of crude base and 2.2 g of (R,R)-tartaric acid, 2.8 g of (R,R)-tartrate, of melting point 157°–159° C. were obtained after recrystallisation in absolute ethanol. The base liberated from this salt takes the form of an oil having a rotatory power $[\alpha]_D^{20} = +42°$ and an optical purity of 97–98%.

EXAMPLE 3

(S)-N,N-dimethyl-N'-benzoyl-N'-(2,3-dihydro-benzofuran-2-ylmethyl)1,3-propanediamine By working as described in Example 1, but starting with 5.2 g of crude base and 2.3 g of (S,S)-tartaric acid, 3.1 g of (S,S)-tartrate of melting point 156°–158° C. were obtained after recrystallisation in absolute ethanol. The base regenerated from this tartrate takes the form of an oil which has a rotatory power $[\alpha]_D^{20} = -42°$ and an optical purity of 97–98%.

The anti-arrhythmic activity of the compounds of the invention was demonstrated in anaesthetised rats by the coronary ligation test according to the procedure of CLARK et al. [Journal of Pharmacological Methods 3, 357–368 (1980)].

The following parameters were recorded every minute for the 30 minutes following ligation.

Ectopic complexes

The assessment is carried out according to the following arbitrary scoring:
0: pure sinus rhythm, or pressure of fewer than 10 ectopic complexes per minute.
1: presence of fewer than 50 ectopic complexes per minute.
2: presence of more than 50 ectopic complexes per minute.

The values shown in the Table below represent the percentage inhibition of ectopic complexes relative to the control group.

Ventricular fibrillation

The number of animals which have shown one or more episodes of ventricular fibrillation lasting more than 5 seconds is noted. The criterion adopted for liminal anti-fibrillating activity is the protection of at least 3 animals out of 6.

The values recorded in the Table represent the number of animals which showed ventricular fibrillation out of a batch of 6 animals.

These results are recorded in the Table below in comparison with those for disopyramide (international common name), a compound known for its anti-arrhythmic activity. The compounds are administered at a dose of 1.25 mg.kg$^{-1}$ intravenously.

TABLE

| Compounds | Ectopic complexes | Ventricular fibrillation |
| --- | --- | --- |
| Example 1 (12309 CERM) | 51% | 4 |
| Example 2 (11901 CERM) | 40% | 2 |
| Example 3 (12304 CERM) | 46% | 2 |
| Disopyramide | 0 | 3 |

These results show that the compounds of the invention possess anti-arrhythmic activities superior to those of disopyramide, the optical isomers being, moreover, of higher activity than the racemic form in respect of ventricular fibrillation.

The compounds of the invention prove, moreover, to possess reduced toxicity: no mortality was observed in mice at 640 mg.kg$^{-1}$ orally.

They may hence be used in human therapy for treating disorders of rhythm.

The compounds of the invention may be administered enterally or parenterally at daily dosages between 0.5 and 15 mg per kg body weight depending on the method of administration. For the treatment of human beings an oral daily dosage of 100 up to 500 mg is preferred.

Mixed with suitable auxiliaries the compounds I or salts thereof may be compressed into solid dosage units such as pills, tablets, coated tablets etc. or may be processed into capsules. By means of suitable liquids the compounds may also be applied as an injection- or oral preparation in the form of solutions, suspensions or emulsions.

These compounds may be administered, for example, in the form of divisible tablets containing 200 mg doses, corresponding to the following unit formula

| | |
| --- | --- |
| Laevorotatory compound: | 200 mg |
| Microcrystalline cellulose: | 70 mg |
| Wheat starch: | 10 mg |
| Polyvinylpyrrolidone: | 6 mg |
| Talc: | 3 mg |
| Magnesium stearate: | 1 mg |
| | 290 mg |

In a planetary mixer, the active principle, microcrystalline cellulose and wheat starch are introduced and carefully mixed, and the mixture is then wetted with a 15% solution of polyvinylpyrrolidone in water and mixed until homogeneous. The mass is then granulated on a 1.60 mm screen and dried in a convection oven at 50° C. After standardisation on a 1.25-mm screen, the talc and magnesium stearate are added, and the components are mixed and then compressed with a rotary press to give a final weight of 290 mg (275.5–304.5) per tablet.

We claim:
1. N,N-dimethyl-N'-benzoyl-N-(2,3-dihydrobenzofuran-2-ylmethyl)1,3-propanediamine of the formula:

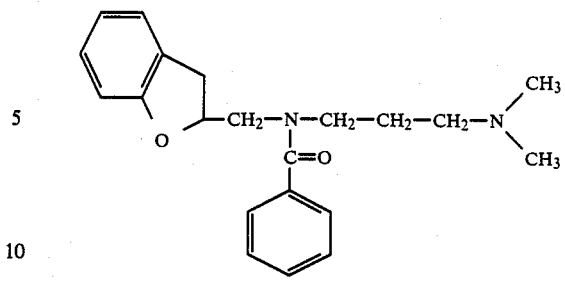

in its enantiomerically pure and mixed forms, and their pharmaceutically acceptable salts.

2. The racemic mixture of compounds according to claim 1, and pharmaceutically acceptable salts thereof.

3. The dextrorotatory isomer according to claim 1, and pharmaceutically acceptable salts thereof.

4. The laevorotatory isomer according to claim 1, and pharmaceutically acceptable salts thereof.

5. Pharmaceutical composition comprising a compound according to claim 1 in an effective amount to provide an antiarrhythmic effect in admixture with one or more usual pharmaceutical carriers.

* * * * *